United States Patent [19]

Ewers et al.

[11] Patent Number: 4,938,938

[45] Date of Patent: Jul. 3, 1990

[54] PROCESS FOR THE PREPARATION OF A HYDROXYL APATITE MATERIAL

[75] Inventors: Rolf Ewers, Graf-Spee-Strasse 46, D-2300 Kiel 1; Christian Kasperk, Bremen; Bruno Simons, Kiel, all of Fed. Rep. of Germany; Bremen

[73] Assignee: Rolf Ewers, Kiel, Fed. Rep. of Germany

[21] Appl. No.: 278,924

[22] PCT Filed: Mar. 24, 1988

[86] PCT No.: PCT/EP88/00247

§ 371 Date: Nov. 22, 1988

§ 102(e) Date: Nov. 22, 1988

[87] PCT Pub. No.: WO88/07498

PCT Pub. Date: Oct. 6, 1988

[30] Foreign Application Priority Data

Mar. 26, 1987 [DE] Fed. Rep. of Germany ....... 3709897

[51] Int. Cl.$^5$ ............................................. C01B 25/32
[52] U.S. Cl. ................................... 423/308; 423/311; 433/201.1; 623/16
[58] Field of Search ............................. 423/308, 311; 433/201.1; 623/16

[56] References Cited

U.S. PATENT DOCUMENTS 3,929,971  12/1975  Roy .
4,861,733  8/1989  White ....................... 501/1

OTHER PUBLICATIONS

Della M. Roy, "Hydroxyapatite Formed From Coral Skeletal Carbonate by Hydrothermal Exchange", *Nature*, vol. 247 (Jan. 25, 1974), pp. 220–222.

Hydrothermal Synthesis of Various Carbonate Containing Calcium Hydroxyapatites, D. M. Roy et al., Mat. Res. Bull., vol. 9, pp. 35–40, 1974, Pergamon Press, Inc.

Petrologic Phase Equilibria, W. G. Ernst, Univ. of Calif., Los Angeles, pp. 27–29, W. H. Freeman and Co., 1976.

Experimental Petrology–Basic Principles and Techniques, Alan D. Edgar, 106–109, Clarendon Press, Oxford, 1973.

*Primary Examiner*—John Doll
*Assistant Examiner*—Wayne A. Lange
*Attorney, Agent, or Firm*—Fleit, Jacobson, Cohn, Price, Holman & Stern

[57] ABSTRACT

A process is disclosed for the preparation of a hydroxyl apatite material by means of hydrothermal conversion using as starting material a calcitic skeleton which has been purified of organic substances. The conversion is carried out under saturated steam pressure, preferably at a temperature in the range of from 100° C. to 250° C. The influence of the reaction, or rather the defect density of the materials is preferably achieved by the addition of fluoride ions. In addition, the adaption of the material to differing implantation areas as hard tissue replacements as well as the preparation of workable compact implants is described.

12 Claims, 1 Drawing Sheet

PROCESS FOR THE PREPARATION OF A HYDROXYL APATITE MATERIAL

The invention relates to a process for the preparation of a carbonaceous hydroxyl apatite material by means of hydrothermal conversion with the addition of an aqueous $(NH_4)_2HPO_4$ solution. As starting material a hard tissue purified from organic substances in employed.

Hydroxyl apatite material of this kind is suitable for use as a biocompatible implant, for examle as hard tissue replacements for bones and teeth, since the inorganic portion of human hard tissue in essence is formed of a cryptocrystalline carbonaceous hydroxyl apatite.

A process is known from U.S. Pat. No. 3,929,971 according to which a hydroxyl apatite material is extracted from the aragonitic skeletons of living corrals and starfish by means of hydrothermal treatment. This known process has the disadvantage that the hydrothermal treatment must be carried out at a relatively high temperature under very high presure.

The use of the hydroxyl apatite material as implants has the disadvantage that, with the known process of production, as a result of the temperature, the pressure and the chemical potential of the participating components, high defect densities do not occur, which results in a bone-like difference of the material from the ideal structure of a dense material of the formula $Ca_{10}(PO_4)_6(OH)_2$ with apatite structure. These defect densities can occur for example by the substitution of carbonate $CO_3^{2-}$ for phosphate $PO_4^{3-}$ or by stray ions, in particular alkali in cation sublattice form, as well as halogenides in the anion sublattice. Moreover, the products obtained by means of the known process do not attaine desired requirements for deviation of the bone-like cryptocrystallinity with respect to the use as implants.

It is an object of the present invention to provide a process of the above type which, as a result of reduced energy requirements and relatively low pressure, can be carried out in a relatively short time and afford the desired bone-like defect density and cryptocrystallinity. desired bone-like defect density and crypytocrystallinity.

Accordingly, the invention provides a process for the preparation of a carbonaceous hydroxyl apatite material by means of hydrothermal conversion with the adddition of aqueous $(NH_4)_2HPO_4$ solution, whereby as starting material an organic substance-free hard tissue is employed, characterized in that the conversion takes place in an autoclave at saturation steam pressure of the respective fluid phase.

Thus, the object is attained by the hydrothermal conversion in an autoclave at saturation stream pressure of the respective fluid phase being employed. The saturation steam pressure is reached if the pressure vessel is not completely filled. Already with operating times of less than 24 hours and a temperature of 200° C., an optimum conversion can be attained.

In a preferred embodiment of thke invention, by means of a controlled adjustment of the pH value of the substitution solution, preferably to at least about 8.5, the formation of other phases than hydroxyl apatite can be suppressed.

In addition, it can also be of advantage to suppress the influence of $Mg^{2+}$ ions by appropriate addition of fluoride ions. This measure has the advantage that the content of magnesium ions compensates for and thereby hinders the formation of undesired $\beta$-tricalcium phosphate ($\beta$-Whitlockite). Furthermore, the crystallinity and defect density of the materials, i.e. the real structure of the material and thus the adaption of the material to the implant area, is attained during the synthesis by the addition of fluoride. This leads to an artifical aging or hardening of the material.

Preferably the process is continued by after-treatment of the hydroxyl apatite material by tempering. Also through these measures can the artificial aging or hardening of the materials be attained. As a result of the temperature, the defect density is influenced, while the crystallite size increases with the tempering time.

In particular, for the preparation of a compact implant, it is advantageous to treat the hydroxyl apatite material with a binding material and thereafter to repeat the previously described steps of the hydrothermal treatment. The material obtained in this manner can be worked with conventional tools.

As an alternative, it is also advantageous that the starting material prior to the hydrothermal treatment should be washed with a binding material, followed by the conversion of the starting material and the binder simultaneously. In this manner, the process can be accelerated.

Slaked lime is preferably employed as the binder, and the hydrothermal treatment is carried out after setting of the lime. For shaping the hydroxyl apatite material, it is expedient that the material be disposed in a mold.

It is particularly preferably to place the hydroxyl apatite material in the mould prior to treatment with slaked lime.

It has also proven very advantageous that, as starting material, the skeletons of lime encrusted algae are used. In this manner, a hydroxyl apatite material is obtained which exhibits an extremely fine surface, porosity and cytophilic surface geometry and which is extremely similar to organogenetic material. By means of the synthesis according to the invention the original interconnecting microporosity of the starting material is retained. In clinical testing, it has been shown that the hydroxyl apatite material obatained herein is not only biocompatible, but also bioactive, and that it is not only integrated in the bone building process, but also active in initiating and supporting osteogenesis.

Alternatively, as starting material an organic, porous hard substance (tissue) is very suitable. The hard substance is advantageously decarbonised prior to conversion.

The invention provides a process which ensures, particularly in the temperature range up to 250° C., and at a pressure of up to 40 bar, an efficient conversion with limited material and energy costs. It stands out above all in contrast to hydrothermal syntheses which require the use of external pressure and need high temperature precious metal containers. Apart from this, bone replacement materials can be obtained, which are bone-like and which in view of their crystallite size and their defect density are excellent for use as implants.

The process will now be further described with reference to a specific example.

First the organic components of the starting material were completely removed. In this way the starting material can be decarbonised at a higher temperature. The following process steps were then carried out:

(1) Cleaning of the starting materials.

(1.1) Separating large grain foreign paricles by the use of binoculars.

(1.2) Repeated washing of the starting material with double distilled water, if necessary at elevated temperature.

(2) Roentgenographic determination of the $Mg^{2+}$ content of the starting material and addition of $F^-$ ions to compensate for the $Mg^+$ content. This compensation can be achieved by the addition of $NH_4F$, alkali fluoride, $CaF_2$, HF or the like.

(3) Synthesis

The starting material is placed in an autoclave having a lining of stable thermoplastic polytetrafluoroethylene (PTFE), and covered with a concentrated aqueous solution of $(NH_4)_2HPO_4$. If required, in order to compensate the $Mg^+$ content a suitable fluoride is added, as already described in paragraph 2. The pH value is then adjusted to about 8.5. The autoclave is not completely filled, so that at elevated temperature, the saturation steam pressue can be accommodated. The maximum temperature is about 250° C. on account of the lining of the autoclave. Already at about 200° C. an optimal conversion can be attained over a time of less than 24 hours.

(4) After-treatment of the material

After the reaction, the pH value is verified (and should have remained unchanged) and the aqueous phase is discarded. The converted hydroxyl apatite material is washed with double distilled water several times and if necessary briefly boiled. Thereafter, the starting material is dried at a temperature above 100° C.

(5) Artificial aging or hardening of the hydroxyl apatite material

The crystallinity and defect density of the material, i.e. the real structure of the material and thereby the adaption of the material to the implantation area, will either be attained by the addition of fluoride in the manner described above during the synthesis, or by tempering of the material at a temperature of up to about 500° C. Thereby on the one hand the temperature of the "carbonate content" of the probe is influenced and by the temper time the crystallite size increases.

(6) Compaction of the hydroxyl apatite material

The converted starting material will be vibratingly placed in a mold or form and treating with slaked lime $(Ca(OH)_2)$. After the setting of the lime, the mold and contents thereof are again subjected to the synthesis steps described in paragraph 3. In this way, the lime-containing binding material is also converted to hydroxyl apatite material.

It is in principle possible to treat the carbonaceous or oxidic starting material directly with binder and in one operation to convert the carbonaceous or oxidic skeleton and the binding material to hydroxyl apatite material. An artificial aging can then follow according to paragraph 5.

By suitable variation in the pressure, the temperature and the chemical potential it is also possible to prepare Whitlockite ($\beta$-$Ca_3(PO_4)_2$).

Very good results can be obtained with the following process steps:

1. Drying the starting material, that can be of calcitic or aragonitic origin.

2. Pyrolizing the materials; linear heating over 6 hours to 750° C., i.e. to a temperature which lies above the decomposition material of the starting material; holding at this temperature for 6 hours; linear cooling over 6 hours. The process technique particularly essential in this procedure is the gradual heating. This pyrolysis step influences the reaction and the product by positively loosening the crystalline packing.

3. Fractionation of the material using a fractionating column.

4. A conventional PTFE-lined autoclave with a volume of 400 ml is filled halfway with the material obtained in the previous process step. A previously prepared solution of 68 g of $(NH_4)_2HPO_4$ and 1 g of $NH_4F$ per 100 ml of $H_2O$ is added to a total filling of the autoclave of 75%. The volume of the autoclave is made large enough so that the concentrated phosphate solution can be added in excess in order to ensure satisfactory saturation during the entire reaction. The excess can easily be calculated empirically.

5. The autoclave is placed in a drying cabinet and left there between 8 and 16 hours at 200° C.

6. The autoclave is then placed in water to effect cooling.

7. The entire autoclave contents are then transferred into an Erlenmeyer flask and rinsed several times with generous quantities of water. Thereafter the product is heated twice with a generous quantity of water 8. Drying is frist carried out under infrared light, then further drying in a drying cupboard at 100° C. and finally for about 4 hours at 200° C., which at the same time effects a dry-sterilization.

As further process steps it is advantageous to subject the material to decarbonization before conversion. After degassing, the pore space opens up and thereby the surface increases.

It is especially important that the phosphate solution be concentrated, that the pH value lies in the basic range, preferably at a minimum of 8.5, and that the solution is employed in excess, based on the material being treated, so that the concentration of the solution does not fall under the previous limit during the entire reaction and the pH value remains in the previously stated desired range. In this manner, a complete conversion to hydroxyl apatite is achieved, without also obtaining traces of Whitlockite. With magnesium-containing calcitic skeletons as starting material, and by the addition of $NH_4F$ in an amount of at least one gram per 100 ml of phosphate solution, a conversion to Whitlockite is prevented. The carbonaceous hydroxyl apatite obtained in this manner affords advantages for clinical application, for example a lower re-absorbability.

Important process parameters are further given in the single figure of the accompanying drawing, which shows graphically the relationship between water and steam for varying pressure and temperature.

An autoclave known per se consists of a closeable, high pressure metal vessel with a screw-fitting or press-fitting, tightly closing, removable cover, in which an adjustable safety valve, a manometer and a thermometer are located. In the bottom of the autoclave is disposed water, which can be heated from the exterior. The steam pressure increases then in the interior up to the value calibrated on the safety valve. Thereafter, the valve opens and the excess pressure is released.

In summary, the invention provides that, on account of the low temperature and the internally supplied pressure generation under minumum deployment of energy, hydroxyl apatite can be produced. The undesired buildup of other phosphates, such as above all Whitlockite, is minimized through the correct establishment and maintenance of a basic pH value. Through the previously given sufficient concentration of phosphate ions in the fluid phase during the entire reaction time, a complete conversion is attained. Furthermore, by the addition of fluoride ions, the presence of magnesium ions is compensated and in this way also the accumulation of undesired phases is reduced. Through the pyrolysis of material according to the invention, the microporosity is maintained. The specific surface is increased through the decarbonization, as well as the fluoridation, compaction and modification of the carbonate content. An external pressure generation is not necessary. Maceration of the material can also be avoided.

What we claim is:

1. A process for the preparation of a carbonaceous hydroxyl apatite material by means of hydrothermal conversion, comprising the following steps:
   (a) cleaning a hard tissue from organic substances,
   (b) converting the tissue with an aqueous concentrated solution of $(NH_4)_2HPO_4$ solution at a temperature up to 250° C.,
   (c) executing the conversion in an autoclave under saturation steam pressure, and
   (d) during conversion compensating for the content of $Mg^{2+}$-ions by addition of F of ions.

2. A process according to claim 1, wherein the pH value of the aqueous solution is adjusted to a predetermined value.

3. A process according to claim 2, wherein the pH value is adjusted to at least 8.5.

4. A process according to claim 1, wherein the hydroxyl apatite material is subjected to an after treatment by tempering.

5. A process according to claim 1, wherein the hydroxyl apatite material is treated with a slurry of a binder material and the indicated process steps for the hydrothermal conversion are then repeated.

6. A process according to claim 5, wherein the binder material is slaked lime and the hydrothermal conversion is carried out after setting of the lime.

7. A process according to claim 5, wherein the hydroxyl apatite material is placed in a mold prior to treatment with the binder material.

8. A process according to claim 1, wherein the hydroxyl apatite material is treated with a slurry of binder material before conversion.

9. A process according to claim 1, wherein the hydroxyl apatite material is placed in a mold.

10. A process according to claim 1, wherein the starting material comprises skeletons of lime-encrusted algae.

11. A process according to claim 1, wherein the starting material comprises an organic, porous hard tissue.

12. A process according to claim 11, wherein the hard tissue is decarbonised prior to the conversion.

* * * * *